United States Patent [19]

Lui et al.

[11] Patent Number: 5,874,655
[45] Date of Patent: *Feb. 23, 1999

[54] PROCESS FOR THE PREPARATION OF CHLORINATED AROMATICS

[75] Inventors: Norbert Lui, Köln; Albrecht Marhold, Leverkusen, both of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 812,197

[22] Filed: Mar. 6, 1997

Related U.S. Application Data

[63] Continuation of Ser. No. 430,986, Apr. 28, 1995, abandoned.

[30] Foreign Application Priority Data

May 5, 1994 [DE] Germany ............................... 4415777.0

[51] Int. Cl.$^6$ .................................................. C07C 19/08
[52] U.S. Cl. ........................................... 570/142; 570/201
[58] Field of Search ................................... 570/173, 201, 570/142

[56] References Cited

U.S. PATENT DOCUMENTS

| | | | |
|---|---|---|---|
| 4,814,524 | 3/1989 | Briody et al. | 570/201 |
| 5,306,849 | 4/1994 | Lui et al. | 570/173 |

FOREIGN PATENT DOCUMENTS

| | | |
|---|---|---|
| 118241 | 9/1984 | European Pat. Off. . |
| 427603 | 5/1991 | European Pat. Off. . |
| 857350 | 10/1952 | Germany . |
| 2931777 | 2/1981 | Germany . |
| 4225763 | 2/1994 | Germany . |

OTHER PUBLICATIONS

W. Coppock, J. Org. Chem, vol, 22, pp. 325–326 (1957).
L. Delaude, et al., J. Org. Chem., vol. 55, pp. 5260–5269 (1990).

*Primary Examiner*—Alan Siegel
*Attorney, Agent, or Firm*—Sprung Kramer Schaefer & Briscoe

[57] ABSTRACT

Chlorinated aromatics are obtained in a simple manner and in particularly good yield if the corresponding chloroformic esters are heated in the liquid phase to 90° to 240° C. in the presence of an inert organic solvent and a catalytic amount of one or more Lewis acids selected from the group consisting of the aluminium halides, iron halides and antimony halides.

9 Claims, No Drawings

PROCESS FOR THE PREPARATION OF CHLORINATED AROMATICS

This application is a continuation of application Ser. No. 08/430,986, filed on Apr. 28, 1995 which is abandoned.

The present invention relates to a liquid-phase process for the preparation of chlorinated aromatics from aromatic esters of chloroformic acid.

It is known that aliphatic esters of chloroformic acid can be thermally converted in the liquid phase in the presence of Lewis acids to give the corresponding chloroalkanes (see DE-A 2 931 777, U.S. Pat. No. 4,814,524 and DE-C 857 350).

Attempts to apply this reaction to aromatic esters of chloroformic acid showed that aromatic esters of chloroformic acid react in a different manner to aliphatic esters of halogenoformic acid. Aromatic esters of chloroformic acid in the presence of aromatic solvents and Lewis acids with heating do not react with decarboxylation to give chlorinated aromatics but react in a Friedel-Crafts reaction to give phenylbenzoates (J. Org. Chem. 22, 325 (1957)). Even if the procedure is carried out in the absence of aromatic solvents, it was therefore to be expected that chlorobenzene possibly formed by decarboxylation immediately reacts with aromatic esters of chloroformic acid still present to give phenylbenzoates and chlorobenzene cannot be isolated.

Other processes for the preparation of substituted chlorinated aromatics are likewise disadvantageous. Thus direct chlorination of alkylaromatics only yields mixtures of isomers which are difficult to separate and frequently contain the desired isomer only in a low proportion (J. Org. Chem. 55, 5260 to 5269 (1990)).

Aromatic esters of chloroformic acid can also be converted to halogenated aromatics in the gas phase in the presence of aluminium oxide which is not coated or coated with noble metals (EP-A 188 241 and 427 603).

Finally, DE-A 42 25 763 discloses that chlorinated aromatics can be prepared from the corresponding esters of chloroformic acid by heating in the presence of hydrogen fluoride or Lewis acids. The yields in this case are between 20 and 74% which is frequently unsatisfactory.

A process has now been found for the preparation of chlorinated aromatics of the formula (I)

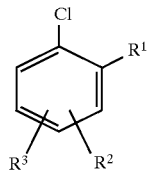  (I)

in which $R^1$ represents $C_1$–$C_6$-alkyl, $R^2$ represents hydrogen or $C_1$–$C_6$-alkyl and $R^3$ represents hydrogen, $C_1$–$C_6$-alkyl, fluorine, chlorine or bromine, which is characterized in that esters of chloroformic acid of the formula (II)

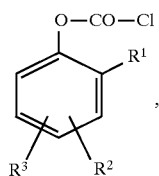  (II)

in which the symbols used have the meaning given under formula (I), are heated in the liquid phase to 90° to 240° C. in the presence of an inert organic solvent and a catalytic amount of one or more Lewis acids selected from the group consisting of aluminium halides, iron halides and antimony halides.

Preferably, in the formulae (I) and (II)

$R^1$ represents straight-chain or branched $C_1$–$C_6$-alkyl or cyclic $C_5$–$C_6$-alkyl, $R^2$ represents hydrogen, straight-chain or branched $C_1$–$C_6$-alkyl or cyclic $C_5$–$C_6$-alkyl and $R^3$ represents hydrogen, straight-chain or branched $C_1$–$C_6$-alkyl, cyclic $C_5$–$C_6$-alkyl, fluorine or chlorine.

Particularly preferably, $R^1$ and $R^2$, independently of each other, represent methyl, ethyl, n-butyl or i-propyl and $R^3$ represents hydrogen or methyl.

It is further preferred that the substituent $R^2$ does not represent hydrogen and the substituents $R^1$ and $R^2$ are present in the 2- and 6-position in relation to chlorine. In these cases, chlorinated aromatics of the formula (I) are obtained in particularly high yields.

The process according to the invention is particularly suitable for the use of 2,6-dimethylphenyl chloroformate.

The chloroformic esters of the formula (II) required as starting compounds to carry out the process according to the intention are known or can be prepared by analogy with known compounds.

Lewis acids selected from the group consisting of aluminium halides, iron halides and antimony halides which are useful are, for example, aluminium trichloride, iron trichloride and aluminium oxide pretreated with hydrogen chloride. To convert the chloroformic esters to chlorinated aromatics, aluminium trichloride is advantageously used.

The Lewis acids can be used e.g. in amounts of 0.01 to 50 mol %, preferably 0.1 to 25 mol %, based on the chloroformic ester of the formula (l).

Preferred inert organic solvents for the process according to the invention are polychlorobenzenes; particular preference is given to tri- and tetrachlorobenzenes such as 1,2,3-trichlorobenzene, 1,2,4-trichlorobenzene and 1,2,4,5-tetrachlorobenzene.

In the batch procedure, the amount of solvent can be e.g. at least 25% by weight of the amount of starting material. There is no upper limit to the amount of solvent. From economic considerations, no more than 10 times the amount by weight of solvent (based on starting material) will generally be used. 50 to 500% by weight of solvent (based on starting material) is preferably used in the batch procedure.

In a continuous procedure the amount of solvent can be decreased, if appropriate. It can be e.g. 2 to 300% by weight, based on the entire amount of starting material introduced in the course of one continuously operated working cycle. This amount is preferably 5 to 30% by weight.

The process according to the invention can be carried out, for example, discontinuously by placing the solvent and the Lewis acid in a reaction vessel and then adding the chloroformic ester at reaction temperature. The procedure can also be carried out continuously, e.g. by continuously feeding the chloroformic ester of the formula (II) into a mixture of solvent and Lewis acid under pressure and temperature conditions such that the chlorinated aromatic of the formula (I) formed continuously distils off.

With regard to the reaction temperature, it must be ensured that within the range of 90° to 240° C. this is selected to be at least as high as the temperature at which the particular starting material begins to decarboxylate. This minimum temperature can, if appropriate, be easily determined by routine preliminary tests. Higher temperatures up to 240° C. can be employed without restrictions.

The pressure while the process according to the invention is carried out must be at least high enough so that the starting material and the solvent are highly predominantly in the liquid phase at the particular reaction temperature. The pressure towards the upwards direction is not critical. It can be, e.g., up to 20 bar.

The work-up in the case of discontinuous procedure can be formed, e.g., in such a way that after completion of gas evolution the chlorinated aromatic formed is distilled out of the reaction mixture. The organic solvent can be recovered, e.g. by distillation, and reused.

The process according to the invention has a number of advantages. It permits the preparation of chlorinated aromatics of the formula (I), in particular of 2,6-dialkylchlorobenzenes in a simple manner (single-stage) and in particularly good yields. It can be carried out in simple apparatuses and at relatively low temperatures. The solvent can be recycled. During the reaction fewer polymers and resinous by-products form in the process according to the invention than in other processes.

It is surprising that in the process according to the invention, despite the presence of Lewis acids, Friedel-Crafts reactions do not proceed or at most proceed to a very minor extent.

EXAMPLES

Example 1

50 g of 2,6-dimethylphenyl chloroformate were added dropwise in 20 min at 190° C. to 235 g of 1,2,3-trichlorobenzene and 2 g of $AlCl_3$. After completion of gas evolution, the 2,6-dimethylchlorobenzene was distilled from the reaction mixture. Yield 94%.

Example 2

2280 g of 2,6-dimethylphenyl chloroformate were added dropwise at 190° C. to 7500 ml of 1,2,4-trichlorobenzene and 50 g of $AlCl_3$ and the 2,6-dimethylchlorobenzene was simultaneously distilled from the reaction mixture. Yield 1690 g (97% of theory) of 2,6-dimethylchlorobenzene.

Example 3

40 g of 2,6-dimethylphenyl chloroformate were added dropwise in 20 min at 195° C. to 433 g of 1,2,4,5-tetrachlorobenzene and 2 g of $AlCl_3$. After completion of gas evolution, the 2,6-dimethylchlorobenzene was distilled from the reaction mixture. Yield 95%.

What is claimed is:

1. A process for the preparation of chlorinated aromatics of the formula (I)

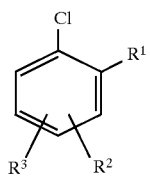

(I)

in which
$R^1$ represents $C_1$–$C_6$-alkyl,
$R^2$ represents hydrogen or $C_1$–$C_6$-alkyl and
$R^3$ represents hydrogen, $C_1$–$C_6$-alkyl, fluorine, chlorine or bromine,
in which an ester of chloroformic acid of the formula (II)

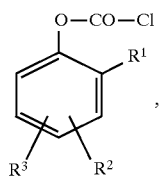

(II)

in which the symbols used have the meaning given under formula (I), is heated in the liquid phase to 90° to 240° C. in the presence of a trichlorobenzene or tetrachlorobenzene and a catalytic amount of one or more Lewis acids selected from the group consisting of aluminum halides, iron halides and antimony halides.

2. The process of claim 1, in which in the formulae (I) and (II)
$R^1$ represents straight-chain or branched $C_1$–$C_6$-alkyl or cyclic $C_5$–$C_6$-alkyl,
$R^2$ represents hydrogen, straight-chain or branched $C_1$–$C_6$-alkyl or cyclic $C_5$–$C_6$-alkyl and
$R^3$ represents hydrogen, straight-chain or branched $C_1$–$C_6$-alkyl, cyclic $C_5$–$C_6$-alkyl, fluorine or chlorine.

3. The process of claim 1, in which in the formulae (I) and (II) the substituent $R^2$ does not represent hydrogen and the substituents $R^1$ and $R^2$ are present in the 2- and 6-position in relation to chlorine.

4. The process of claim 1, in which 0.01 to 50 mol % of Lewis acids selected from the group consisting of aluminium halides, iron halides and antimony halides are used per mole of chloroformic ester of the formula (II).

5. The process of claim 1, in which the reaction temperature is at least as high as the temperature at which the particular starting material begins to decarboxylate.

6. The process of claim 1, in which the pressure is at least high enough so that the starting material and the solvent are situated highly predominantly in the liquid phase at the particular reaction temperature.

7. The process according to claim 1, in which after completion of the reaction the chlorinated aromatics formed of the formula (I) are separated off from the reaction mixture by distillation.

8. The process of claim 1, in which the particular chloroformic ester of the formula (II) is fed continuously into a mixture of the polychlorobenzene and Lewis acid and the chlorinated aromatic formed of the formula (I) is continuously distilled off.

9. The process of claim 1, in which 2,6-dimethylphenyl chloroformate is used.

* * * * *

UNITED STATES PATENT AND TRADEMARK OFFICE
CERTIFICATE OF CORRECTION

PATENT NO. : 5,874,655
DATED : February 23, 1999
INVENTOR(S) : Lui, et al.

It is certified that error appears in the above-identified patent and that said Letters Patent is hereby corrected as shown below:

| | |
|---|---|
| Title Page | ABSTRACT: Line 6 delete " aluminium and substitute -- aluminum -- |
| Col. 1, line 39 | Delete " aluminium and substitute -- aluminum -- |
| Col. 2, line 13 | Delete " aluminium " and substitute -- aluminum -- |
| Col.. 2, line 38-39 | Delete " aluminium " and substitute -- aluminum -- |
| Col. 2, line 40 | Delete " aluminium " and substitute -- aluminum -- |
| Col. 2, line 41 | Delete " aluminium " and substitute -- aluminum -- |

UNITED STATES PATENT AND TRADEMARK OFFICE
CERTIFICATE OF CORRECTION

PATENT NO.   : 5,874,655
DATED        : February 23, 1999
INVENTOR(S)  : Lui, et al.

It is certified that error appears in the above-identified patent and that said Letters Patent is hereby corrected as shown below:

Col. 2, line 43          Delete " aluminium " and substitute
                         -- aluminum --

Col. 4, claim 4          Delete " aluminium " and substitute
lines 2-3                -- aluminum --

Signed and Sealed this

Fourteenth Day of December, 1999

Attest:

Q. TODD DICKINSON

*Attesting Officer*    Acting Commissioner of Patents and Trademarks